United States Patent

Roberts et al.

(10) Patent No.: US 6,926,673 B2
(45) Date of Patent: Aug. 9, 2005

(54) OPTICAL TRACKING SYSTEMS

(75) Inventors: Patricia Roberts, Romsey (GB); Ed Sparks, Southampton (GB); Chris Harris, Romsey (GB)

(73) Assignee: Roke Manor Research Limited, Romsey (GB)

( * ) Notice: Subject to any disclaimer, the term of this patent is extended or adjusted under 35 U.S.C. 154(b) by 98 days.

(21) Appl. No.: 10/432,867
(22) PCT Filed: Nov. 28, 2001
(86) PCT No.: PCT/GB01/05272
§ 371 (c)(1),
(2), (4) Date: Oct. 29, 2003
(87) PCT Pub. No.: WO02/44749
PCT Pub. Date: Jun. 6, 2002

(65) Prior Publication Data
US 2004/0100557 A1 May 27, 2004

(30) Foreign Application Priority Data
Nov. 28, 2000 (GB) .............................................. 0028939
Oct. 11, 2001 (GB) .............................................. 0124423

(51) Int. Cl.7 ................................................. A61B 8/14
(52) U.S. Cl. ...................................... 600/464; 600/472
(58) Field of Search ................................ 600/407, 424, 600/429, 437, 459–472; 606/130; 128/916, 920, 922

(56) References Cited

U.S. PATENT DOCUMENTS

| | | | |
|---|---|---|---|
| 5,792,147 A | | 8/1998 | Evans et al. |
| 5,924,989 A | | 7/1999 | Polz |
| 6,193,657 B1 | * | 2/2001 | Drapkin ...................... 600/437 |
| 6,216,029 B1 | * | 4/2001 | Paltieli ........................ 600/427 |
| 6,398,731 B1 | * | 6/2002 | Mumm et al. ............... 600/437 |
| 6,684,098 B2 | * | 1/2004 | Oshio et al. ................. 600/429 |
| 6,755,791 B2 | * | 6/2004 | Kawashima ................. 600/467 |
| 6,801,801 B1 | * | 10/2004 | Sati ............................ 600/429 |

FOREIGN PATENT DOCUMENTS

| | | |
|---|---|---|
| GB | 2 246 261 A | 1/1992 |
| WO | WO 98 08112 A | 2/1998 |
| WO | WO 00 63658 A | 10/2000 |
| WO | WO00 63719 A | 10/2000 |

* cited by examiner

Primary Examiner—Ali Imam
(74) Attorney, Agent, or Firm—Crowell & Moring LLP

(57) ABSTRACT

A method of tracking the position and orientation of an ultrasound beam emitted from an ultrasound probe. The method includes the steps of storing a model of the visible object in a memory of an optical tracking system; calculating the position and orientation of the visible object; and calculating the position and orientation of the ultrasound beam by applying a known geometric relationship to the deduced position and orientation of the visible object.

9 Claims, 2 Drawing Sheets (a)

(b)

(c)

(d)

(e)

(f)

OPTICAL TRACKING SYSTEMS

This application is the U.S. National Phase under 35 U.S.C. § 371 of International Application PCT/GB01/05272, filed Nov. 28, 2001, which claims priority of United Kingdom 0028939.7, filed Nov. 28, 2000 and United Kingdom 0124423.5, filed Oct. 11, 2001.

The present invention relates to optical tracking systems. More particularly, it relates to optical tracking devices allowing the location of certain objects to be calculated, which objects cannot themselves be optically tracked.

For example, when an ultrasound probe is in use, possibly for the production of a three-dimensional ultrasound image, the ultrasound beam cannot itself be visually tracked, as it is invisible. In another situation, an ultrasound probe may be used for industrial non-destructive testing. This will encounter the same problems of invisibility of the ultrasound beam.

The present invention therefore addresses these problems and aims to provide optical tracking methods and apparatus for equipment, such as probes, for which the locations of the points of measurement or the points of effect, such as ultrasound beams, are not directly measurable, but are in a known geometric relationship to a part of the equipment whose position and orientation can be measured.

The present invention accordingly provides a method for tracking the position and orientation of an ultrasound beam emitted from an ultrasound probe, the ultrasound beam bearing a geometric relationship to a visible object, comprising the steps of: storing a model of the visible object in a memory of an optical tracking system; calculating the position and orientation of the visible object; and calculating the position and orientation of the ultrasound beam by applying the geometric relationship to the deduced position and orientation of the visible object.

The position and orientation of the visible object may itself comprise the steps of: estimating a position and orientation of the visible object; generating an estimated image of the visible object in the estimated position and orientation; comparing the estimated image with a video image of the visible object, and adjusting the estimated image by adjusting the estimated position and orientation, until the estimated image corresponds to the video image, thereby deducing the actual position and orientation of the visible object.

The calculated position and orientation of the ultrasound beam may be expressed in co-ordinates expressed with respect to an observer. The method may then further comprise the step of translating the calculated position and orientation into a position and orientation expressed with reference to an object under test.

The method may farther comprise a calibration step in which the geometric relationship between the ultrasound beam and the visible object is deduced.

The visible object may comprise a visually distinct object, being one of: a marker attached to a visible part of the probe; visual markings on the surface of the probe; or the shape and profile of the probe itself.

A plurality of ultrasound beams may be simultaneously tracked.

In an embodiment of the invention, the probe is a scanning ultrasound probe producing two-dimensional images, the ultrasound beam is planar and the visible object is a visible part of the probe, wherein: the probe is moved across an object to be scanned; the position and attitude of the probe is measured and recorded as a function of time; images produced by the probe are recorded as a function of time; and the recorded positions, attitudes and images are combined to produce a three dimensional image of the scanned object.

A further probe may also be tracked, in which case the relative position and orientation of the ultrasound beam and the point of effect of the further probe may each be calculated.

In such an embodiment of the present invention, the further probe may be a biopsy needle. The method may then comprise moving the ultrasound probe across a body to be scanned; measuring the position and attitude of the ultrasound probe; measuring the position and attitude of the biopsy needle; calculating the positions and attitudes of the ultrasound beam and the tip of the biopsy needle; and displaying the position of the biopsy needle on the image provided by the ultrasound scanner.

These, and other, features, characteristics and advantages of the present invention will become more apparent with reference to the following description of certain embodiments of the present invention, given by way of examples only, with reference to the accompanying drawings in which.

In order to track the location of the point of measurement or the point of effect of equipment such as probes, the position and orientation of a part of the equipment whose position and orientation can be measured may be tracked. The required point of measurement or effect can then be calculated if it bears a known geometric relationship to the position and orientation of the part of the equipment whose position and orientation can be measured.

In an example, the position and orientation of a handle of a biopsy needle may be tracked, and the position and orientation of the point of effect, at the end of the needle, may be calculated according to the known geometry of the needle.

A three-dimensional video tracking system may be employed to determine the position and orientation of a visible part of the equipment. An example of a suitable system is described in UK Patent GB 2 246 261. The system described in that document involves the comparison of a modelled image, based on a previously stored model of the tracked object in conjunction with an assumed location and orientation of the object, with a video image of the object. By calculating the differences in position of various reference points on the model and the corresponding points on the video image, the actual position and orientation of the tracked object may be calculated. As described in that document, the modelled image may be adjusted until it matches the video image. Alternatively, as described therein with reference to aircraft navigation, the position (flight path) of the observer (video camera) may be adjusted until the video image matches the modelled image. By repeatedly comparing the images and adjusting the modelled image, the location and orientation of the equipment may be tracked.

Other types of video tracking system may be employed in the system of the present invention, but the system used must be able to use data from video imagery to continuously track, and calculate the position and orientation of, visually distinct rigid objects for which 3D models are available.

The visually distinct object tracked by a tracking system may be: a marker attached to the visible part of the equipment (such as a probe); visual markings such as a printed pattern or symbol on the surface of the equipment; or the shape and profile of the equipment itself.

A probe may be powered, in which case a light emitting means such as one or more LED's may be attached to it, and the light emitting means may be used as a marker for tracking the position and orientation of the probe. Alternatively, an unpowered probe may be used, and ambient or directed light may be employed to illuminate the object, to render visible the marker, markings or shape and profile of the probe.

Figure 1:
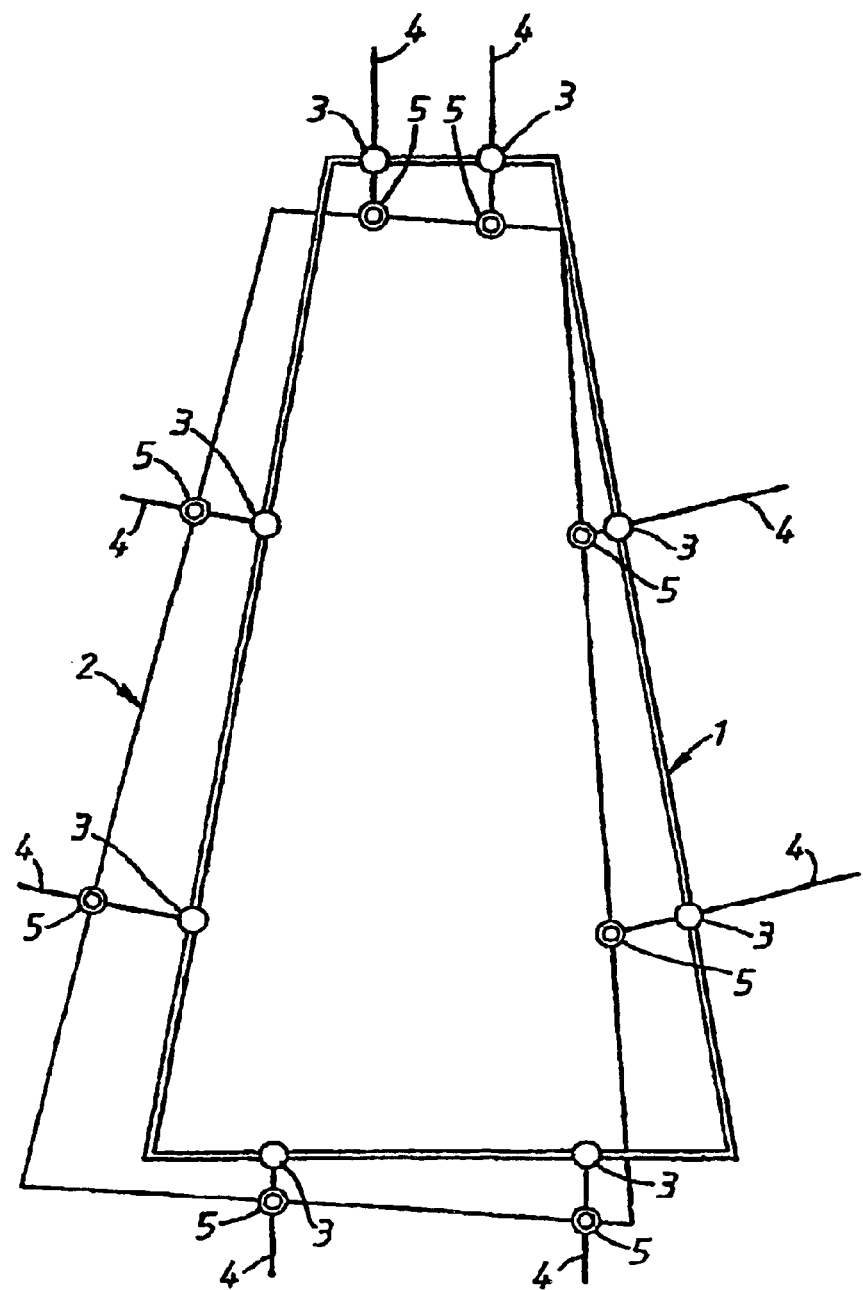
FIG. 1 shows a modelled image and a video image of a tracked object.
Figure 2:
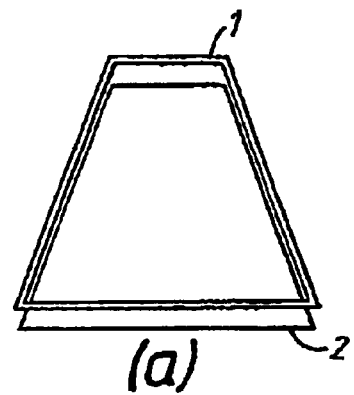
FIG. 2 shows possible differences between the modelled image and the observed video image.
Figure 2:
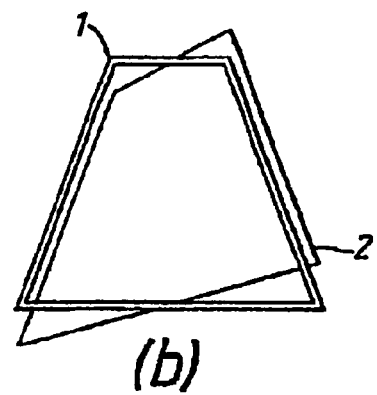
Figure 2:
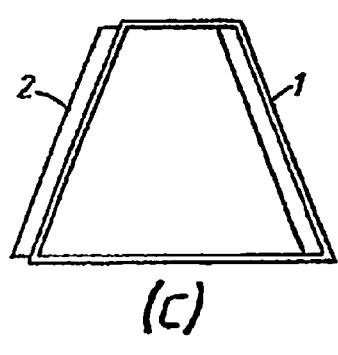
Figure 2:
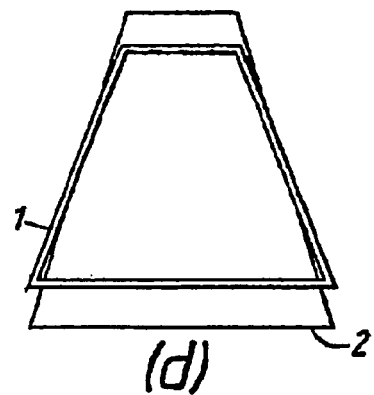
Figure 2:
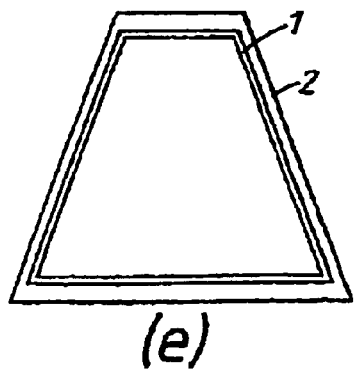
Figure 2:
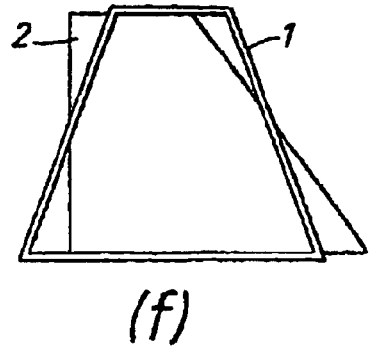

FIG. 1 schematically shows a modelled image 1 and a video image 2 of a handle of a biopsy needle. In the present case, the profile of the handle itself is used as the marker. Four visible corners may be used as reference points, calculating intermediate reference points 3, 5 in the modelled and video images, respectively.

The orientation and dimensions of the modelled image is adjusted until it matches the observed video image. FIGS. 2(a) to 2(f) illustrate various possible differences between the modelled image and the observed video image. These represent, respectively: (a) the true position of the handle is lower than the modelled estimated position; (b) the true position of the handle is rolled to the left of the modelled estimated position; (c) the true position of the handle lies to the left of the modelled estimated position; (d) the true orientation of the handle is pitched up from the modelled estimated position; (e) the true position of the handle is nearer than the modelled estimated position; and (f) the true orientation of the handle is yawed to the left of the modelled estimated position of the handle.

The differences between the locations of respective reference points 3, 5 in the modelled and true images are then reduced by recalculating the modelled estimated image until the two images match. The location and orientation of the handle is then known, in three dimensions. Since the point of interest, that is, a point of measurement or point of effect of a needle or probe or the like, bears a known three-dimensional geometric relationship to the position and orientation of the handle, the position and orientation of the point of interest may be simply calculated.

This will, however, provide the position of interest only in the co-ordinate system of the observer, that is, relative to the position of the video camera. It will not provide the position of the point of interest with relation to the object under examination.

For example, it is of limited use to know that the point of measurement or point of effect is at so many millimetres in each of x, y and z directions from the camera, if one cannot also deduce which part of an object is being acted upon, for example, from which part of a body an autopsy needle is taking a tissue sample.

The optical tracking system used in the present invention may also track the position and orientation of the object under inspection, and may then use this tracking to locate the point of interest in the object's co-ordinate system, as will be described in more detail below.

It may be necessary to employ more than one camera in the optical tracking system, to improve measurement accuracy. In some embodiments, the optical tracking system may track more than one piece of equipment (e.g. probe), and may then calculate the relative positions and orientations of the probes.

While the present invention enables the orientation and location of any type of equipment to be deduced, it has particular application to the tracking of probes in medical and industrial testing environments.

The following types of probe could be used in embodiments of the present invention.

(i) Point probes, such as temperature probes, pH probes, needles and syringes, which act at a single point. The system of the present invention is used to determine the location of the probe tip.

(ii) Axial probes, such as single angle ultrasound probes, which act in one dimension, along a line emanating from the location of the probe. The system of the present invention is used to determine the location of the line of the probe.

(iii) Planar probes such as scanned angle ultrasonic probes, which act in two dimensions, across a plane emanating from the location of the probe. The system of the present invention is used to determine the location and orientation of the plane of the probe.

(iv) Three-dimensional probes, such as CT or magneto-resonance imaging (MRI) probes, act in all directions from the probe, but the orientation of the probe must be accurately known in order to make sense of the measurements provided by the probe. The system of the present invention is used to determine the location and orientation of the volume covered by the probe.

Hence, the point of measurement or point of effect which is to be located may be three dimensional (volume), two dimensional (plane), one dimensional (line), or without dimension (point).

The desired result of tracking a probe is usually that the position of the point of measurement or point of effect may be determined in a desired co-ordinate system. A first stage in this is to find the position of the point of measurement or effect in the co-ordinate system of the camera. To achieve this, a calibration must be performed to find the geometric relationship between the point of measurement or effect and the visually distinct object, so that the measurement of the marker position can be used to find the position of the point of interest. A correlation must therefore be determined between the three dimensional position of the visually distinct object, and the position of the point of measurement or point of effect, which may itself be a point, line, plane or volume, as discussed above.

For point probes and axial probes, calibration may be carried out automatically, for example using a process in which the tip (point of measurement or point of effect) of the probe is held fixed, and the probe is moved around it, while the visually distinct object is tracked by the optical tracking system. From the measurements of the position of the visually distinct object, the location of the tip with respect to the visually distinct object may be deduced.

With particular reference to the present invention, for axial and planar ultrasound probes, calibration can be carried out by accepted ultrasound calibration techniques.

A registration process may need to be carried out, to find the relationship between the camera co-ordinate system and the co-ordinate system for the object under test, so that measurements made by the cameras can be reported in the object's co-ordinate system. Any known point-based registration process may be used, whereby the positions of known points on the object are measured in camera co-ordinates, these being matched to measurements of the same points in the object co-ordinates, and the transformation between these sets of points is then found. Typically, this operation would be carried out at the start of each test.

Alternatively, the transformation between camera coordinates and object co-ordinates may be found opportunistically by measuring the probe position throughout the test, whenever it is in contact with the inspected object. Surface reflection may be employed to determine when the probe is in contact with the surface. With knowledge of the position of the active point of the probe with respect to the tracked visually distinct object, a model of the surface of the object under test can be reconstructed, which is then matched to a model of the object in the object co-ordinate system (such as a CAD model) to calculate the transformation between the two sets of co-ordinates.

Certain specific examples of implementation of the present invention, along with the particular advantages arising from these implementations, will now be discussed.

Three-dimensional (3D) ultrasound scanning is a growing field. Data is collected from a planar probe, and corresponds to two-dimensional ultrasound scans, representing slices through the object. The data from these slices is processed to give an overall three dimensional representation of the object. This representation may be viewed from any desired angle, to provide a much clearer impression of the structure of the object than would be possible from the slice data alone. In order for this three-dimensional processing to be effective, the position and orientation of the ultrasound probe must be known at all times during data collection, so that the data can be reassembled into 3D form. Many of the methods currently used for probe position measurement are less than satisfactory, and an optical tracking system according to the present invention may improve the efficiency of probe position measurement, and so improve the clarity and reliability of the three-dimensional images produced.

In an embodiment of the present invention, an ultrasound probe is moved across the object to be scanned. An optical tracking system, such as described in itself above, will measure the position and attitude of the ultrasound probe, and this will be recorded as a function of time. The two-dimensional ultrasound scans will also be recorded as a function of time. This information will allow the three dimensional scanned volume to be reconstructed as an image.

An ultrasound guided biopsy technique is known, for extracting tissue from a patient with minimal intrusion. An operator, usually a radiologist, scans the patient using ultrasound, views the site for biopsy, and guides the biopsy needle to the correct position. However, it has been found difficult to see the biopsy needle on the scan. The present invention may be applied to track both the ultrasound probe and the biopsy needle, allowing the position of the biopsy needle to be displayed on the ultrasound scan image.

Operation of such a system will involve the following steps: the ultrasound probe will be moved across the patient to produce a scan image, while the biopsy needle is held in approximately the correct position, as judged by the radiologist. An optical tracking system, as described in itself above, will track both the probe and the biopsy needle and measure their positions and attitudes. Using calibrations, as discussed above, for each of the probe and the biopsy needle, the position of the needle axis and tip can be calculated in the scan co-ordinate system and displayed on the scan image as a graphical overlay. This allows the operator to guide the tip of the biopsy needle to the exact point required for sampling, regardless of whether the patient changes position during the process.

Ultrasound scanning is used in industrial non-destructive testing. Typically, an ultrasound operator manually records the position of the probe when defects were found, and later calculates the defect location from knowledge of the probe characteristics, the timing of the ultrasound signal, and the speed of sound in the tested material. In an embodiment of the present invention, an optical tracking system, as described in itself above, is used to automate the recording process, so reducing errors and the time taken. Measurements of the probe position may be recorded by the optical tracking system, to ensure that the object has been fully scanned for defects.

The operator will move the ultrasound probe across the object under test. The optical tracking system will track the probe, and measure its position and orientation. The operator will indicate when a defect is discovered, and this data will be recorded. Using the probe calibration, calculated as described above, the positions of defects can then be found in the camera co-ordinate system. This measurement can then be translated into the required location of the defect within the object using the registration procedure described above.

While the present invention has been particularly described with reference to a certain number of specific embodiments, given by way of example only, the invention may be applied in various modified forms.

For example, while the invention may be applied to tracking the position of features obscured by reason of their insertion into a body, the invention may also be applied to tracking the position of features which cannot be directly tracked, either due to their being invisible; or their being obscured by other pieces of equipment; or simply because the feature in question cannot be clearly detected by a visual tracking system.

What is claimed is:

1. A method for tracking the position and orientation of an ultrasound beam emitted from an ultrasound probe, the ultrasound beam bearing a geometric relationship to a visible object, comprising the steps of:
   storing a model of the visible object in a memory of an optical tracking system;
   calculating the position and orientation of the visible object; and
   calculating the direction of propagation of the ultrasound beam by applying the geometric relationship to the deduced position and orientation of the visible object,
   wherein the step of calculating the position and orientation of the visible object itself comprises the steps of:
      estimating a position and orientation of the visible object;
      generating an estimated image of the visible object in the estimated position and orientation;
      comparing the estimate image with a video image of the visible object; and
      adjusting the estimated image by adjusting the estimated position and orientation, until the estimated image corresponds to the video image, thereby deducing the actual position and orientation of the visible object.

2. A method according to claim 1 wherein the direction of propagation of the ultrasound beam is expressed in coordinates expressed with respect to an observer.

3. A method according to claim 2, further comprising the steps of translating the calculated direction of propagation into a direction of propagation expressed with reference to an object under test.

4. A method according to claim 1, further comprising a calibration step in which the geometric relationship between the ultrasound beam and the visible object is deduced.

5. A method according to claim 1 wherein the visible object comprises a visually distinct object, being one of: a marker attached to a visible part of the probe; visual markings on the surface of the probe; or the shape and profile of the probe itself.

6. A method according to claim 1 wherein a plurality of ultrasound beams are simultaneously tracked.

7. A method according to claim 1 wherein the probe is a scanning ultrasound probe producing two-dimensional images, the ultrasound beam is planar and the visible object is visible part of the probe, wherein:

the probe is moved across an object to be scanned;

the position and attitude of the probe is measured and recorded as a function of time;

images produced by the probe are recorded as a function of time; and the recorded positions, attitudes and images are combined to produce a three dimensional image of the scanned object.

8. A method according to claim 1 wherein a further probe is tracked, and the relative direction of propagation of the ultrasound beam and the point of effect of the further probe is calculated.

9. A method according to claim 8 wherein the further probe is a biopsy needle, and wherein:

the ultrasound probe is moved across a body to be scanned;

the position and attitude of the ultrasound probe is measured;

the position and attitude of the biopsy needle is measured;

the direction of propagation of the ultrasound beam and the position and orientation of the tip of the biopsy needle are calculated; and the position of the biopsy needle is displayed on the image provided by the ultrasound scanner.

* * * * *